US012588836B2

(12) United States Patent
Hochmuth et al.

(10) Patent No.: US 12,588,836 B2
(45) Date of Patent: Mar. 31, 2026

(54) METHOD FOR THE PREPARATION OF A WORKING ELECTRODE

(71) Applicant: Roche Diabetes Care, Inc., Indianapolis, IN (US)

(72) Inventors: Gernot Hochmuth, Mannheim (DE); Kirill Sliozberg, Mannheim (DE); Alexander Steck, Hirschberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 744 days.

(21) Appl. No.: 17/931,419

(22) Filed: Sep. 12, 2022

(65) Prior Publication Data

US 2023/0000398 A1     Jan. 5, 2023

Related U.S. Application Data

(63) Continuation of application No. PCT/EP2021/056437, filed on Mar. 13, 2021.

(30) Foreign Application Priority Data

Mar. 13, 2020     (EP) ..................................... 20162941

(51) Int. Cl.
*A61B 5/145*          (2006.01)
*G01N 27/327*        (2006.01)
(52) U.S. Cl.
CPC .........  *A61B 5/145* (2013.01); *G01N 27/3272* (2013.01); *A61B 2562/125* (2013.01)
(58) Field of Classification Search
None
See application file for complete search history.

(56) References Cited

U.S. PATENT DOCUMENTS 9,880,126 B2     1/2018  Kim et al.
2004/0182719 A1     9/2004  Purvis et al.
(Continued)

FOREIGN PATENT DOCUMENTS

EP        2 119 795 A1     11/2009
EP        2697388 A1      2/2014
(Continued)

OTHER PUBLICATIONS

International Search Report and Written Opinion of the International Searching Authority, PCT/EP2021/056437, May 27, 2021, 15 pages.
(Continued)

*Primary Examiner* — J. Christopher Ball
(74) *Attorney, Agent, or Firm* — Bose McKinney & Evans LLP

(57)          ABSTRACT

A method of preparing a working electrode on a sensor substrate is disclosed. A sensor substrate is provided and has a first side with at least one conductive trace. A layer of sensing material is applied onto the first side and covers at least a portion of the at least one conductive trace. The sensing material is irradiated with a laser beam to partially remove the layer of the sensing material while preserving a portion of the sensing material covering the at least one conductive trace, resulting in a working electrode on the sensor substrate. A membrane layer is applied that at least partially covers the working electrode. The membrane layer includes a cross-linker that cross-links at least a part of the sensing material. A diffusion step is performed during which the cross-linker in the membrane layer at least partially diffuses into the sensing material.

12 Claims, 2 Drawing Sheets

(56)                    References Cited

U.S. PATENT DOCUMENTS

| | | | |
|---|---|---|---|
| 2005/0239154 A1* | 10/2005 | Feldman | A61B 5/14532 |
| | | | 435/14 |
| 2007/0135698 A1 | 6/2007 | Shah et al. | |
| 2008/0179187 A1 | 7/2008 | Ouyang et al. | |
| 2009/0156920 A1 | 6/2009 | Kotzan et al. | |
| 2010/0230285 A1 | 9/2010 | Hoss et al. | |
| 2014/0054171 A1 | 2/2014 | Feldman et al. | |
| 2022/0057355 A1 | 2/2022 | Jeong et al. | |

FOREIGN PATENT DOCUMENTS

| | | | |
|---|---|---|---|
| JP | 2009-519106 A | 5/2009 | |
| JP | 2010-517054 A | 5/2010 | |
| JP | 2012-519038 A | 8/2012 | |
| JP | 2019-078573 A | 5/2019 | |
| JP | 2021-525371 A | 9/2021 | |
| RU | 2004 104 334 A | 4/2005 | |
| WO | WO 01/36660 A2 | 5/2001 | |
| WO | WO 2005/078424 A1 | 8/2005 | |
| WO | WO 2006/018447 A2 | 2/2006 | |
| WO | WO 2007/071562 A1 | 6/2007 | |
| WO | WO 2007/147475 A1 | 12/2007 | |
| WO | WO 2010/028708 A1 | 3/2010 | |
| WO | WO 2010/099507 A1 | 9/2010 | |
| WO | WO 2012/130841 A1 | 10/2012 | |
| WO | WO 2014/001382 A1 | 1/2014 | |
| WO | WO 2019/166394 A1 | 9/2019 | |

OTHER PUBLICATIONS

Feldman et al., "A Continuous Glucose Sensor Based on Wired Enzyme Technology—Results from a 3-Day Trial in Patients with Type 1 Diabetes," Diabetes Technology & Therapeutics, 2003, vol. 5, No. 5, pp. 769-779.

Liu et al., "Miniature Amperometric Self-Powered Continuous Glucose Sensor with Linear Response," Analytical Chemistry, 2012, vol. 84, No. 7, pp. 3403-3409.

* cited by examiner

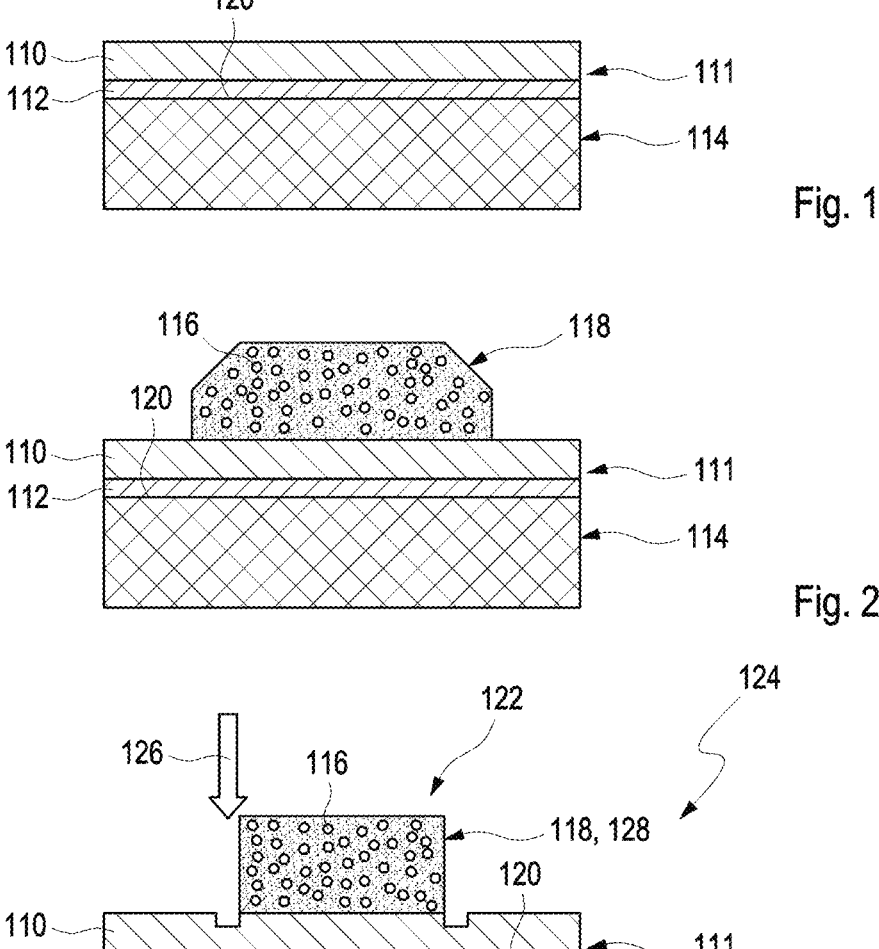
Fig. 1
Fig. 2
Fig. 3
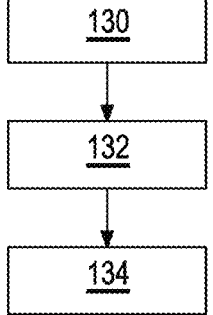
Fig. 4

METHOD FOR THE PREPARATION OF A WORKING ELECTRODE

RELATED APPLICATIONS

This application is a continuation of PCT/EP2021/056437, filed Mar. 13, 2021, which claims priority to EP 20 162 941.7, filed Mar. 13, 2020, both of which are hereby incorporated herein by reference.

BACKGROUND

This disclosure generally relates to a method for the preparation of a working electrode and to an analyte sensor comprising the working electrode, as well as to the use of the analyte sensor for detecting at least one analyte in a sample. In particular, this disclosure relates to a method for the preparation of a working electrode, the method comprising laser irradiation.

Monitoring certain body functions, more particularly monitoring one or more concentrations of certain analytes, plays an important role in the prevention and treatment of various diseases.

Along with so-called point measurements in which a sample of a body fluid is specifically taken from a user and investigated for the analyte concentration, continuous measurements are increasingly becoming available. Hence, there is an increasing demand for accurate analyte sensors that enable reliable and cost-efficient analyte detection from a body fluid or other samples. An analyte sensor for determining the concentration of an analyte under in-vivo conditions is known from WO 2010/028708 A1. Another example of such sensor is disclosed in WO 2012/130841 A1. Moreover, WO 2007/147475 A1 discloses an amperometric sensor configured for implantation into a living body to measure the concentration of an analyte in a body fluid. An alternative sensor element is disclosed in WO 2014/001382 A1.

In the manufacturing of commercially available analyte sensors, a structuring step is required to form the layer of the sensing material on the substrate of the sensor such as continuous or long-term glucose monitoring sensors. Current ways of conducting this structuring step involve screen printing, dip-coating, and dispensing methods.

These methods are disadvantageous in that the sensing material cannot be applied sufficiently homogenously onto the sensor substrate such that inhomogeneities occur, in particular at the edges of the sensor substrate. These so called edge effects lead to varying sensor sensitivity across charges. In order to reduce sensor signal sensitivity variation across different charges detailed monitoring and fine adaptation of the manufacturing parameters is required. This can be time consuming and expensive.

WO 2006/018447 discloses a method for the preparation of electrode assemblies for use in an electrochemical sensor. In this method, conductive layers are applied to a dielectric substrate and conductive traces are formed by laser ablation. No details on the application of the layer of sensing material to the working electrode are given.

U.S. Pat. No. 9,880,126 discloses a biosensor and a method for its production. The sensor comprises a carbon layer, which may be prepared by laser ablation. No details on the application of a layer of sensing material to the working electrode are given.

WO 2010/099507 A1 discloses methods and systems for providing continuous analyte monitoring including in vivo sensors that do not require any user calibration during in vivo use. Furthermore, it discloses methods of manufacturing the no-calibration sensors and post manufacturing packaging and storage techniques.

JP 2019078573 discloses a biosensor manufacturing method which reduces sensitivity of a biosensor during manufacturing thereof without depending on the concentration of a measurement object component. In the biosensor manufacturing method, an electrode layer of the biosensor which includes an electrode system including at least an action electrode and a counter electrode is formed on an insulating substrate, and a detection layer which contains a component reacting with a measurement object component is formed on the electrode layer. At least the detection layer is scraped after the detection layer is formed.

U.S. Publication No. 2014/0054171 A1 discloses an analyte sensor configured to utilize oxygen as an oxidant and method for manufacturing and using the same. The analyte sensor includes a catalyst to facilitate use of oxygen as oxidant. The catalyst may be provided on an electrode of the analyte sensor.

Feldmann et al., Diabetes Technology & Therapeutics, Vol. 5, No. 5, 2003, 769-780 discloses study using 48 sensors implanted for three days. Prospective calibration was performed using capillary blood.

EP 2 119 795 A1 relates to a single use disposable electrode strip for attachment to the signal readout circuitry of a sensor system to detect a current representative of an analyte in an aqueous medium.

SUMMARY

This disclosure teaches a method for the preparation of an analyte sensor that avoids the above-mentioned disadvantages. In particular, this disclosure teaches a preparation method resulting in a homogenous sensing material structure on the working electrode such that the need for detailed monitoring and fine adaptation of manufacturing parameters is avoided or at least significantly reduced. It is further advantageous to provide an analyte sensor, which has high and reproducible sensitivity across charges but can be manufactured at low cost, e.g., by using the preparation process disclosed herein that avoids detailed monitoring and fine adaptation of manufacturing parameters.

The method according to this disclosure is advantageous as it allows the manufacturing of a working electrode which may be comprised in an analyte sensor with high and reproducible sensor sensitivity across charges. Further, the sensitivity can be selected and precisely adjusted during the manufacturing. Since detailed monitoring and fine adaptation of manufacturing parameters can be avoided, costs may be reduced and factory calibration of the sensor is possible. Additionally, the sensor drift can be reduced.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "substrate," "layer," "conductive trace," and "electrode," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

According to this disclosure, a method for the preparation of a working electrode on a sensor substrate is disclosed. The working electrode may be part of an analyte sensor.

The method comprises the following steps, which specifically may be performed in the given order. Further, two or more process steps may be performed simultaneously or partially simultaneously. Further, one or more than one or even all of the method steps may be performed once or more than once or even repeatedly or continuously. The method may further comprise additional method steps, which are not listed. The method comprises the following steps:

a) providing at least one sensor substrate comprising at least a first side, the first side comprising at least one conductive trace;

b) applying at least one layer of at least one sensing material onto the first side of the sensor substrate, wherein the sensing material covers at least a portion of the at least one conductive trace; and c) irradiating the layer of the sensing material with at least one laser beam, wherein at least a first portion of the layer of the sensing material is at least partially removed and wherein at least a second portion of the sensing material covering the at least one conductive trace is preserved on the first side of the sensor substrate to obtain at least one working electrode on the sensor substrate.

A further aspect of this disclosure is a method for the preparation of a working electrode (122) on a sensor substrate (114), the method comprising:

a) providing at least one sensor substrate (114) comprising at least a first side (120), the first side (120) comprising at least one conductive trace (111);

b) applying at least one layer of at least one sensing material (118) onto the first side (120) of the sensor substrate (114), wherein the sensing material (118) covers at least a portion of the at least one conductive trace (111); and c) irradiating the layer of the sensing material with at least one laser beam, wherein at least a first portion of the layer of the sensing material (118) is at least partially removed and wherein at least a second portion of the sensing material (118) covering the at least one conductive trace (111) is preserved on the first side (120) of the sensor substrate (114) to obtain at least one working electrode (122) on the sensor substrate (114), e) applying at least one membrane layer, the membrane layer at least partially covering the working electrode (122), wherein the membrane layer comprises at least one cross-linker for cross-linking at least a part of the sensing material (118), wherein the method further comprises:

f) at least one diffusion step, wherein in the diffusion step the cross-linker comprised in the membrane layer at least partially diffuses into the sensing material (118).

The embodiments and preferences described in the following apply to both of the above-described methods.

The term "working electrode" as used herein, is a broad term and is to be given its ordinary and customary meaning to a person of ordinary skill in the art and is not to be limited to a special or customized meaning. The term specifically may refer, without limitation, to the electrode of the analyte sensor that is sensitive for the analyte. The working electrode may be disposed on the at least one sensor substrate comprising the at least one first side. In particular, the working electrode comprises at least one conductive trace and at least one layer of at least one sensing material disposed onto the conductive trace on the first side of the sensor substrate. The sensing material may cover at least a portion of the at least one conductive trace. A first portion of the layer of the sensing material may be laser-irradiated with at least one laser beam, such that a second portion of the sensing material covering the conductive trace is preserved on the first side (120) of the sensor substrate (114), wherein said second portion of the sensing material in conjunction with the conductive trace forms at least one working electrode. The working electrode may be comprised in an analyte sensor. The analyte sensor typically comprises additionally a further electrode, such as, for example, a counter electrode and/or a reference electrode. The layer of sensing material may be present on the working electrode only and may typically be absent from any further electrodes, e.g., the counter electrode and/or the reference electrode may not comprise a layer of the sensing material.

In addition, this disclosure discloses a method for the preparation of an analyte sensor. The method for the preparation of an analyte sensor comprises the method for the preparation of a working electrode on a substrate as disclosed herein and a step of providing at least one further electrode.

The analyte sensor may be configured for at least partial implantation, specifically transcutaneous insertion, into a body tissue of a user, more specifically the analyte sensor may be configured for continuous monitoring of the analyte, even more specifically the analyte sensor may be configured for continuous glucose monitoring.

The terms "user" and "subject" are used interchangeably herein. The terms may in particular relate to a human being.

The term "analyte sensor" as used herein is a broad term and is to be given its ordinary and customary meaning to a person of ordinary skill in the art and is not to be limited to a special or customized meaning. The term specifically may refer, without limitation, to an arbitrary element or device configured for detecting or for measuring the concentration of the at least one analyte. The analyte sensor specifically may be an analyte sensor suitable for at least partial implantation into a body tissue of a user, more specifically an analyte sensor for continuous monitoring of the analyte.

The analyte sensor of this disclosure is an electrochemical sensor comprising the working electrode obtainable according to the method of this disclosure and at least one further electrode and respective circuitry. More particularly, the sensor is an amperometric electrochemical sensor comprising the at least one working electrode. Typically, the analyte sensor comprises at least one further electrode, particularly a counter electrode and/or a reference electrode or a combined counter/reference electrode. The working electrode is sensitive for the analyte to be measured at a polarization voltage which may be applied between working and reference electrodes and which may be regulated by a potentiostat. A measurement signal may be provided as an electric current between the counter electrode and the working electrode. A separate counter electrode may be absent and a pseudo reference electrode may be present, which may also work as a counter electrode. Thus, an analyte sensor typically may comprise a set of at least two, in an embodiment a set of three electrodes. In an embodiment, the analyte sensor comprises precisely two electrodes, in particular precisely one working electrode and one combined counter/reference electrode. Particularly, the sensing material is present in the working electrode only.

Particularly, the analyte sensor according to this disclosure may be fully or a partially implantable and may, thus, be adapted for performing the detection of the analyte in the body fluid in a subcutaneous tissue, in particular, in an interstitial fluid. Other parts or components may remain outside of the body tissue. For example, as used herein, the terms "implantable" or "subcutaneous" refer to be fully or at least partly arranged within the body tissue of the user. For this purpose, the analyte sensor may comprise an insertable portion, wherein the term "insertable portion" may generally refer to a part or component of an element configured to be insertable into an arbitrary body tissue while counter electrode and/or reference electrode or the combined counter/reference electrode may remain outside of the body tissue. Preferably, the insertable portion may fully or partially comprise a biocompatible surface, which may have as little detrimental effects on the user or the body tissue as possible, at least during typical durations of use. For this purpose, the insertable portion may be fully or partially covered with at least one biocompatibility membrane layer, such as at least one polymer membrane, for example, a gel membrane which, on one hand, may be permeable for the body fluid or at least for the analyte as comprised therein, and may on the other hand be impermeable for compounds comprised in the analyte sensor, in particular in the working electrode, thus preventing a migration thereof into the body tissue. Further details regarding the biocompatibility membrane layer are disclosed elsewhere herein.

Further, the term "analyte" as used herein is a broad term and is to be given its ordinary and customary meaning to a person of ordinary skill in the art and is not to be limited to a special or customized meaning. The term specifically may refer, without limitation, to an arbitrary element, component or compound which may be present in a body fluid and the concentration of which may be of interest for a user. Specifically, the analyte may be or may comprise an arbitrary chemical substance or chemical compound which may take part in the metabolism of the user, such as at least one metabolite. As an example, the at least one metabolite may be selected from the group consisting of glucose, cholesterol, triglycerides, lactate, ketones, urea, creatinine, glutamate, ethanol, ascorbic acid, choline, acetylcholine, polyphenol, monophenols, dihydroxyphenols, bisphenol A (BPA) and hydrochlorothiazide (Hct); more specifically the analyte may be glucose. Additionally or alternatively, however, other types of analytes and/or any combination of analytes may be determined, such as a concentration of an electrolyte, or a pO2, pCO2, pH, or Hb value, which indicates a concentration of oxygen, carbon dioxide, hydrogen, or hemoglobin, respectively.

Even further, the term "sensor substrate" as used herein, is a broad term and is to be given its ordinary and customary meaning to a person of ordinary skill in the art and is not to be limited to a special or customized meaning. The term specifically may refer, without limitation, to any kind of material or combination of materials which is suitable to form a carrier layer to support the conductive traces and/or the layer of sensing material as described herein. In particular, a "sensor substrate" as understood herein may comprise electrically insulating material.

The term "layer," as used herein, is a broad term and is to be given its ordinary and customary meaning to a person of ordinary skill in the art and is not to be limited to a special or customized meaning. The term specifically may refer, without limitation, to an element of a layer setup of the analyte sensor. Specifically, the term "layer" may refer to an arbitrary covering of an arbitrary substrate, specifically of a flat substrate. The layer may specifically have a lateral extension exceeding its thickness by at least a factor of 2, at least a factor of 5, at least a factor of 10, or even at least a factor of 20 or more. Specifically, the analyte sensor may have a layer setup. The analyte sensor may comprise a plurality of layers such as the at least one conductive trace, the at least one layer of the at least one sensing material, at least one membrane layer. One or more of the layers of the analyte sensor may comprise sub-layers. For example, a layer comprising the conductive trace may comprise at least one further layer.

The term "electrically insulating material," as used herein, is a broad term and is to be given its ordinary and customary meaning to a person of ordinary skill in the art and is not to be limited to a special or customized meaning. "Electrically insulating material" may also refer to a dielectric material. The term specifically may refer, without limitation, to a material or combination of materials which prevent the transfer of electrical charges and which do not sustain a significant electrical current. Specifically, without limiting other possibilities, the at least one electrically insulating material may be or may comprise at least one insulating resin, such as insulating epoxy resins used in manufacturing electronic printed circuit boards; in particular it may comprise or be a thermoplastic material such as polycarbonate, polyester like polyethylene terephthalate (PET), polyvinyl chloride (PVC), polyurethane, polyether, polyamide, polyimide or a copolymer thereof, such as glycol modified polyethylene terephtalate; Polyethylene naphthalate, Polytetrafluoroethylene or alumina.

In the method and in the analyte sensor according to this disclosure, the sensor substrate may comprise two opposing sides, at least a first side and at least a second side opposing the first side.

Specifically, the analyte sensor, more specifically the sensor substrate, may additionally comprise at least one further electrode, wherein the at least one further electrode may comprise at least one of a reference electrode and a counter electrode. In an embodiment, the at least one further electrode comprises a combined counter/reference electrode. In particular, the reference electrode may comprise at least one reference electrode conductive trace; and/or the counter electrode may comprise at least one counter electrode conductive trace. It is to be understood that in case the further electrode comprises a combined counter/reference electrode the embodiments and preferences described with regard to the reference electrode conductive trace and the counter electrode conductive trace apply mutatis mutandis to the conductive trace of the combined counter/reference electrode. More specifically, the at least one further electrode may be disposed on at least one of: the first side and the second side opposing the first side of the sensor substrate.

The term "conductive trace," as used herein, is a broad term and is to be given its ordinary and customary meaning to a person of ordinary skill in the art and is not to be limited to a special or customized meaning. The term specifically may refer, without limitation, to an electrically conductive strip, layer, wire or other type of elongated electrical conductor. More specifically, the term "conductive trace" may refer, without limitation, to a material which is electrically conductive and hence capable of sustaining an electrical current, for example, the conductive trace may comprise at least one material selected from the group consisting of: carbon; carbon paste; gold; copper; silver; nickel; platinum; palladium. Specifically, the conductive trace may be or may comprise at least one metal, such as one or more of gold, copper, silver, nickel, palladium or platinum. Additionally or alternatively, the at least one conductive trace may be or may comprise at least one electrically conductive compound, such as at least one electrically conductive organic or inorganic compound. Additionally or alternatively, the at least one conductive trace may be or may comprise at least one nonmetallic electrically conductive material, e.g., polyaniline, Poly-3,4-ethylenedioxythiophene (PEDOT), carbon or carbon paste. Carbon paste specifically may relate to a material comprising carbon, a solvent such as diethylene glycol butyl ether, and at least a binder such as vinyl chloride co- and terpolymers. Preferably, the conductive trace according to this disclosure may comprise gold and/or carbon; more preferably the conductive trace may consist of gold and/or carbon. Specifically the conductive trace may comprise gold and a further material, for example, carbon.

Moreover, the conductive trace may comprise at least one further layer of at least one further material, specifically the further layer may comprise a further electrically conductive material. More specifically the further layer of the conductive trace may comprise or may consist of carbon. The further layer may be disposed on the first side. Using a further layer comprising or consisting of carbon in the conductive trace on the sensor substrate may be advantageous as it may enhance the attachment of the layer of the sensing material on the conductive trace. Moreover, in the case of carbon, the further material may contribute to efficient electron transfer by the conductive trace.

The conductive trace may have a thickness of at least 0.1 μm, preferably of at least 0.5 μm, more preferably of at least 5 μm, specifically of at least 7 μm, or at least 10 μm. In the case where the conductive trace comprises carbon or is carbon, the conductive trace may specifically have a thickness of at least 7 μm, more specifically of at least 10 μm. Specifically, in the case where the conductive trace is gold, the conductive trace may have a thickness of at least 100 nm, more specifically of at least 500 nm.

A minimum thickness as specified above may be advantageous as it ensures proper electron transport. A thickness below the specified values is usually not sufficient for reliable electron transport. Even more specifically the thickness should not exceed a value of 30 μm in the case of carbon and a value of 5 μm in the case of gold. If the thickness is too large, the overall thickness and hence the size of the analyte sensor may increase. Larger analyte sensor sizes are generally unwanted as they may cause difficulties when being implanted.

The terms "reference electrode conductive trace" and "counter electrode conductive trace," as used herein, are broad terms and are to be given its ordinary and customary meaning to a person of ordinary skill in the art and are not to be limited to a special or customized meaning. The terms specifically may refer, without limitation, to an electrically conductive strip, layer, wire or other type of elongated electrical conductor present on a reference electrode or a counter electrode, respectively. More specifically, the terms may refer, without limitation, to a material which is electrically conductive and hence capable of sustaining an electrical current, for example, the reference electrode conductive trace and/or the counter electrode conductive trace may comprise at least one material as specified herein above with respect to the conductive trace. In addition to the materials listed above, the reference electrode conductive trace and/or the counter electrode conductive trace may specifically comprise Ag/AgCl.

The term "sensing material," as used herein, is a broad term and is to be given its ordinary and customary meaning to a person of ordinary skill in the art and is not to be limited to a special or customized meaning. The term specifically may refer, without limitation, to a material that may be or may comprise at least a polymeric material; specifically it may be or may comprise at least a polymeric material and at least a metal containing complex. The metal containing complex may be selected from the group of transition metal element complexes, specifically the metal containing complex may be selected from osmium-complexes, ruthenium-complexes, vanadium-complexes, cobalt-complexes, and iron-complexes, such as ferrocenes, such as 2-aminoethyl-ferrocene. Even more specifically, the sensing material may be a polymeric transition metal complex as described, for example, in WO 01/36660 A2, the content of which is included by reference. In particular, the sensing material may comprise a modified poly (vinylpyridine) backbone loaded with poly(bi-imidizyl) Os complexes covalently coupled through a bidentate linkage. The sensing material is further described in Feldmann et al, Diabetes Technology & Therapeutics, 5 (5), 2003, 769-779, the content of which is included by reference. Suitable sensing materials further may include ferrocene-containing polyacrylamide-based viologen-modified redox polymer, pyrrole-2,2'-azino-bis(3-ethylbenzthiazoline-6-sulfonic acid)(ABTS)-pyrene, Naphthoquinone-LPEI. The polymeric transition metal complex may represent a redox mediator incorporated into a cross-linked redox polymer network. This is advantageous as it may facilitate electron transfer between the at least one enzyme or analyte and the conductive trace. In order to avoid a sensor drift, the redox mediator and the enzyme may be covalently incorporated into a polymeric structure.

In an embodiment the sensing material may comprise a polymeric material and MnO2-particles.

The sensing material may, in addition, comprise at least one enzyme; specifically the enzyme is capable of catalyzing a chemical reaction consuming at least the analyte; specifically the enzyme may be an $H_2O_2$ generating and/or consuming enzyme; even more specifically a glucose oxidase (EC 1.1.3.4), a hexose oxidase (EC 1.1.3.5), an (S)-2 hydroxy acid oxidase (EC 1.1.3.15), a cholesterol oxidase (EC 1.1.3.6), a glucose dehydrogenase, a galactose oxidase (EC 1.1.3.9), an alcohol oxidase (EC 1.1.3.13), an L-glutamate oxidase (EC 1.4.3.11) or an L-aspartate oxidase (EC 1.4.3.16); even more specifically a glucose oxidase (GOx) and/or modifications thereof.

Moreover, the sensing material may additionally comprise at least one crosslinker; the crosslinker may, for example, be capable of cross-linking at least part of the sensing material. Specifically the sensing material may comprise at least one crosslinker selected from UV-curable crosslinkers and chemical crosslinkers; more specifically the sensing material comprises a chemical crosslinker. Alternatively, the sensing material may be free of any crosslinker. "Free of any crosslinker" as used herein, is a broad term and is to be given its ordinary and customary meaning to a person of ordinary skill in the art and is not to be limited to a special or customized meaning. The term specifically may refer, without limitation, to the situation that no crosslinker is present in the sensing material during step b) of applying to the first side of the senor substrate. More specifically, "free of crosslinker" may refer to a concentration of 0-0.5 wt-% based on the dry weight of the sensing material. The term "dry weight" as used herein refers to the dry matter of the respective material, e.g., the material without the addition of any water or other solvent. Specifically, the sensing material may be free of crosslinker during step b) but a crosslinker may be added to the sensing material later during the production process, e.g., by diffusion from the membrane layer as explained herein below. Suitable chemical crosslinkers according to this disclosure are selected from: epoxide based crosslinkers, such as diglycidyl ethers like poly(ethylene glycol) diglycidyl ether (PEG-DGE) and poly (propylene glycol) diglycidyl ether; trifunctional short chain epoxides; anhydrides; diglycidyl ethers such as Resorcinol diglycidyl ether, Bisphenol A diglycidyl ether, Diglycidyl 1,2-cyclohexanedicarboxylate, Poly(ethylene glycol) diglycidyl ether, Glycerol diglycidyl ether, 1,4-Butanediol diglycidyl ether, Poly(propylene glycol) diglycidyl ether, Bisphenol diglycidyl ether, Poly(dimethylsiloxane), diglycidyl ether, Neopentyl glycol diglycidyl ether, 1,2,7,8-Diepoxyoctane, 1,3-Glycidoxypropyl-1,1,3,3-Tetramethyldisioxane; triglycidyl ethers such as N,N-Diglycidyl-4-glycidyloxyaniline, Trimethylolpropane triglycidyl ether; tetraglycidyl ethers such as Tetrakisepoxy cyclosiloxane, Pentaerythritol tetraglycidyl ether, tetraglycidyl-4,4'-methylenebisbenzenamine.

The term "chemical crosslinker" as used herein, is a broad term and is to be given its ordinary and customary meaning to a person of ordinary skill in the art and is not to be limited to a special or customized meaning. The term specifically may refer, without limitation, to a crosslinker that is capable of initiating a chemical reaction generating a cross linked molecular network and/or a cross-linked polymer when exposed to heat. "Exposed to heat" may refer to being exposed to a temperature above 15° C., specifically to a temperature above 20° C.; more specifically to a temperature in the range from 20° C. to 50° C. and even more specifically to a temperature in the range from 20° C. to 25° C. More specifically, chemical crosslinkers may initiate cross linking of the layer of the sensing material when exposed to heat.

The term "UV-curable" as used herein, is a broad term and is to be given its ordinary and customary meaning to a person of ordinary skill in the art and is not to be limited to a special or customized meaning. The term specifically may refer, without limitation, to the ability of a chemical substance, for example, a crosslinker, of initiating a photochemical reaction generating a cross linked molecular network and/or a cross linked polymer when irradiated by light in the UV spectral range. More specifically, UV-curable crosslinkers may initiate cross linking of the layer of the sensing material when irradiated by UV light. Cross linking may in particular be initiated as indicated herein below.

Suitable UV curable crosslinkers according to this disclosure include: benzophenone, diazirine and azide. Particularly suitable UV-curable crosslinkers are, for example, selected from the group consisting of, benzophenone comprising cross-linkers, poly(di(2-hydroxy 3 aminobenzophenonepropylene) glycol), Dibenzophenone 1,2-cyclohexanedicarboxylate, Bis[2-(4-azidosalicylamido)ethyl] Disulfide, reaction products of the reaction of 4-aminobenzophenone with any one of the above for the chemical cross-linker described diglycidyl cross-linkers, triglycidyl cross-linkers and tetraglycidyl cross-linkers, an example of such a reaction product is 2,4,6,8-Tetramethyl-2,4,6,8-tetrakis(2-hydroxy 3-aminpropylbenzophenone)-cyclotetrasiloxan, and reaction products of the reaction of 4-Benzoyl-benzoic Acid N-Succinimidyl Ester with a diamin or a jeffamin.

UV-curable crosslinkers are particularly useful and advantageous according to this disclosure as they do not alter the viscosity properties of the sensing material during the step b) of applying the at least one layer of the sensing material. Similarly, viscosity properties remain unchanged in cases where no crosslinker is present in the sensing material. Consistent viscosity properties of the sensing material may allow a more even and homogenous application of the layer of the sensing material during manufacturing and hence may reduce inhomogeneities and edge effects on the sensor surface that may otherwise occur. Reducing inhomogeneities and edge effects may result in reproducible sensor sensitivity across charges. The use of a sensing material comprising no crosslinker or a UV-curable cross-linker may hence contribute to reduce the requirement of detailed monitoring and fine adaptation of manufacturing parameters during production.

The sensing material may at least comprise a polymeric transition metal complex, an enzyme capable of catalyzing a chemical reaction consuming at least the analyte, particularly an $H_2O_2$ generating and/or consuming enzyme, and optionally a crosslinker. Specifically, the sensing material may comprise at least a polymeric transition metal complex and GOx and optionally a chemical crosslinker. More specifically, the sensing material may comprise a modified poly (vinylpyridine) backbone loaded with poly(bi-imidizyl) Os complexes covalently coupled through a bidentate linkage, GOx and optionally a chemical crosslinker like poly(ethylene glycol) diglycidylether (PEG-DGE). Suitable further sensing materials are known to the person skilled in the art and specified herein above.

The sensing material according to this disclosure may, for example, comprise 60 wt % of a polymeric transition metal complex; 30-40 wt % of an enzyme capable of catalyzing a chemical reaction consuming at least the analyte, particularly a $H_2O_2$ generating and/or consuming enzyme, and 0-10 wt % of a crosslinker based on the total weight of the sensing material. The enzyme may, for example, be present at a concentration of 50 mg/ml in water.

The method according to this disclosure may, in particular, additionally comprise at least one curing step d), wherein in the curing step at least a part of the sensing material is cross-linked. The terms "cross linking" and "curing" are interchangeably used herein. Specifically, the curing step d) may take place prior to laser irradiation in step c) or alternatively, at least partially after performing step c).

Suitable ways for initiating cross linking depend on the type of crosslinker and are known by the person skilled in the art. Curing using UV-curable crosslinkers is generally induced by irradiation using UV light. As used herein, the term "UV light" generally refers to electromagnetic radiation in the ultraviolet spectral range. The term "ultraviolet spectral range" generally refers to electromagnetic radiation in the range of 1 nm to 380 nm, preferably light in the range of 100 nm to 380 nm. The curing usually may take place at room temperature.

The applying of the sensing material in step b) may comprise using at least one coating process. As further used herein, the term "coating process" may refer to an arbitrary process for applying at least one layer to at least one surface of an arbitrary object. The applied layer may cover the object, for example, the conductive trace and/or the sensor substrate completely or may only cover a part or parts of the object. The layer may be applied via a coating process wherein a material is provided, e.g., in a liquid form, exemplarily as a suspension or as a solution, and may be distributed on the surface. Specifically, the coating process may comprise a wet-coating process selected from the group consisting of: spin-coating; spray-coating; doctor-blading; printing; dispensing; slot-coating; dip-coating. Specifically step b) may comprise using doctor blading or slot—coating. The sensing material in step b) may further be applied in a way that at least 5%, at least 10%, at least 30%, of the surface of the conductive trace is covered; specifically 5 to 100%, more specifically 5% to 40% of the surface of the conductive trace is covered.

The method according to this disclosure comprises step c) of irradiating the sensing material with at least one laser beam, wherein at least the first portion of the layer of the sensing material is at least partially removed and wherein at least the second portion of the sensing material covering the at least one conductive trace is preserved on the first side of the sensor substrate to obtain at least one working electrode of the analyte sensor. The term "irradiating" as used herein, is a broad term and is to be given its ordinary and customary meaning to a person of ordinary skill in the art and is not to be limited to a special or customized meaning. The term specifically may refer, without limitation, to a process of exposing the layer of the sensing material to laser light. In particular, the first portion is irradiated with at least one laser beam and the second portion is preferably not irradiated with the at least one laser beam. Specifically, step c) may comprise at least one ablation process, in particular at least one laser ablation process. The term "first portion," as used herein, is a broad term and is to be given its ordinary and customary meaning to a person of ordinary skill in the art and is not to be limited to a special or customized meaning. The term specifically may refer, without limitation, to a part of the layer of the sensing material in an outer region. More specifically, the first portion may be a part of the layer of the sensing material contributing to edge effects and/or inhomogeneities. In particular, the first portion is part of the layer of the sensing material which is irradiated with the at least one laser beam. The term "second portion the layer of the sensing material," as used herein, is a broad term and is to be given its ordinary and customary meaning to a person of ordinary skill in the art and is not to be limited to a special or customized meaning. The term specifically may refer, without limitation, to a central part of the layer of the sensing material. In particular, the second portion is not irradiated with the at least one laser beam.

The term "removed," as used herein, is a broad term and is to be given its ordinary and customary meaning to a person of ordinary skill in the art and is not to be limited to a special or customized meaning. The term specifically may refer, without limitation, to ablated parts of the layer of the sensing material, specifically to the first portion. The removed parts may typically be aspirated by techniques known to the person skilled in the art. The term "partially removing," as used herein, is a broad term and is to be given its ordinary and customary meaning to a person of ordinary skill in the art and is not to be limited to a special or customized meaning. The term specifically may refer, without limitation, to complete removing of the first portion, wherein embodiments are possible in which ≥70%, preferably ≥80% and more preferably ≥90% of the first portion is removed. The partially removing of the first portion may comprise removing parts of the conductive trace. The partially removing of the first portion may comprise removing parts of the second portion, too. Preferably, only the first portion is at least partially removed.

In case removing of the first portion of the layer of the sensing material comprises removing parts of the conductive trace, it is possible to remove the conductive trace in the region of the first portion of the layer of the sensing material fully or partially, preferably fully. Thus, in an embodiment wherein the conductive trace is removed fully in the region of the first portion of the layer of the sensing material after the removing of the first portion, the second portion of the layer of the sensing material and the conductive trace may have the same size. In an embodiment, in which the conductive trace comprises at least one further layer, for example, the conductive trace comprises gold and the further layer comprises carbon, during the removing of the first portion of the layer of the sensing material it is possible to additionally remove only the first portion of the further layer but not the other parts of the conductive trace.

Therefore, in an embodiment of this disclosure, the method for the preparation of a working electrode on a sensor substrate comprises the following steps:

a1) providing at least one sensor substrate comprising at least a first side, the first side comprising at least one conductive trace, in particular the conductive trace comprises gold and/or carbon, in particular the conductive trace comprises at least one further layer of at least one further material, in particular the at least one further layer comprises carbon;

b1) applying at least one layer of at least one sensing material onto the first side of the sensor substrate wherein the sensing material covers at least a portion of the at least one conductive trace, in particular the at least one further layer; and c1) irradiating the layer of the sensing material with at least one laser beam wherein at least a first portion of the layer of the sensing material and at least a first portion of the conductive trace, in particular of the further layer, is at least partially removed and wherein at least a second portion of the sensing material covering the at least one conductive trace, in particular the further layer, and a second portion of the conductive trace, in particular of the further layer, are preserved on the first side of the sensor substrate to obtain at least one working electrode.

For the first portion and the second portion of the conductive trace, in particular of the further layer, the embodiments and preferences as described above for the first portion and the second portion of the layer of the sensing material apply. Furthermore, the embodiments and preferences described below and above for the inventive method apply also to the method in which also conductive trace is removed.

Removing also a first portion of the conductive trace, in particular of the further layer is advantageous as it reduced the background current of the sensor comprising the working electrode.

The term "preserved," as used herein, is a broad term and is to be given its ordinary and customary meaning to a person of ordinary skill in the art and is not to be limited to a special or customized meaning. The term specifically may refer, without limitation, to maintained second portion and/or remaining second portion of the layer of the sensing material. The second portion may be or may comprise a patterned layer. The term "patterned layer" as used herein is a broad term and is to be given its ordinary and customary meaning to a person of ordinary skill in the art and is not to be limited to a special or customized meaning. The term specifically may refer, without limitation, to a surface of one or more of the further layer comprised in the at least one conductive trace or the at least one layer of the at least one sensing material that has been patterned by the irradiation with the laser beam. Specifically, with a laser beam under conditions specified herein. The terms "patterned layer" and "laser-patterned layer" are interchangeably used herein. In particular, the term "patterned layer" refers to at least a part of the surface of the layer of the sensing material and/or of the further layer of the conductive trace that has been patterned using the laser beam. More specifically, the "patterned layer" corresponds to the second portion. Thus, the patterned layer is the part of the sensing material which is not removed and preferably not irradiated by the laser beam. Therefore, the patterned layer can be obtained by irradiating the layer of the sensing material and/or the sensor substrate with a laser beam at conditions specified herein. By ablation patterned layers with any kind of shape and/or structure can be realized. Even patterned layers comprising letters or a chess board like structure may be possible.

For example, the layer of the sensing material may have before step c) a thickness of 1 to 4 μm. By irradiating the sensing material with the laser beam the first portion may be ablated from the layer of the sensing material thereby generating or forming a patterned layer on the sensor substrate. The patterned layer may then corresponds to the second portion.

The term "to obtain at least one working electrode," as used herein, is a broad term and is to be given its ordinary and customary meaning to a person of ordinary skill in the art and is not to be limited to a special or customized meaning. The term specifically may refer, without limitation, to forming and/or manufacturing the working electrode.

The term "laser ablation" may generally refer to arbitrary processes of removing at least a part of a material from a surface by irradiating the surface punctually with a laser beam. Thereby, the material may be removed. The material may be at least partially destroyed, e.g., by sublimation due to the transfer of energy. A transfer of energy, e.g., heat, may be locally limited. As an example, for the purpose of laser ablation, a pulsed laser may be used. Energy of a pulse may be in the range of less than 40 μJ. Specifically, the laser may be configured for irradiating the layer of sensing material using ultra short laser pulses such that the first portion is removed within a very short period of time so that diffusion of heat into the preserved second portion is minimized. The pulse length may be limited to less than 12 ps. For example, the laser may be configured for generating a laser beam in the UV spectral range. Specifically, a laser having a wavelength of 355 nm may be used. As an example, for the purpose of laser ablation, a frequency tripled solid state laser emitting at a wavelength of 355 nm with a pulse duration of less than 12 ps and with a pulse repetition rate of 400 kHz may be used. In step c) at least one ablation pattern may be used. The ablation pattern may be provided as a mask image that is projected onto the layer of sensing material. The ablation pattern may alternatively be drawn by scanning the laser beam across the layer of sensing material. For example, the layer of sensing material may be irradiated using at least one scanning process. The term "scanning" as used herein, is a broad term and is to be given its ordinary and customary meaning to a person of ordinary skill in the art and is not to be limited to a special or customized meaning. The term specifically may refer, without limitation, to continuous or pulsed irradiation of the layer of sensing material during generation of the patterned layer with a specific scanning velocity. The ablation rate may depend on pulse energy, laser wavelength, pulse length, pulse repetition rate, beam diameter on the irradiated surface, scanning velocity, pulse overlap, overlap of adjacent scanning lines, spectral absorption coefficient of the irradiated material and ablation threshold of the irradiated material. Specifically the term "ablation rate" may refer to the thickness of the ablated material. For example, in the case of laser ablation using a mask, the ablation rate may refer to the entire mask image. In this case, the ablation rate may be particularly dependent on the pulse energy, the irradiated surface area, and/or the threshold value for ablation of the material, for example, the energy required for removing the material. In the case of laser ablation by a scanning process, the ablation rate for the entire image may depend on the properties of the laser including the laser wavelength, pulse energy, pulse rate; in combination with the properties of the optical system such as beam diameter on the surface of the material; in combination with the settings of the laser including overlap of the laser pulse, e.g., overlap of the pulse along the scanning line and line overlap, e.g., overlap of neighboring scan lines; and the properties of the irradiated material, e.g., the sensing material, including coefficient of absorption and ablation threshold.

During or subsequent to the ablation process ablated material may be removed by any process known in the art such as by using at least one dust extractor or the like.

Specifically, the layer of the second portion of the sensing material has a thickness of at least 0.5 μm. More specifically, a thickness of 0.5 to 5 μm, even more specifically a thickness of 1 to 4 μm. Still even more specifically the values refer to the thickness of the dried matter after partial removal by irradiating with a laser beam. The specified thickness may be advantageous as it may ensure sufficient amount of electron transfer over a broad range of analyte concentrations Thicknesses below and/or above the described values are disadvantageous as they may result in suboptimal electron transfer and glucose conversion.

The method according to this disclosure may further comprise an additional step bb) of drying the at least one layer of the at least one sensing material. Specifically, the layer of the sensing material is dried prior to step c) of irradiating the layer of sensing material with a laser beam. A drying step prior to step c) is advantageous as it enables precise removal of at least a part of the layer of the sensing material in step c). If the layer of sensing material is not sufficiently dry, the partial removal of sensing material by laser irradiation will not be efficient and less precise. The drying step bb) may take place at ambient temperature. Specifically, the sensing material may be dried at ambient temperature for 0.5 to 15 minutes. The term "ambient temperature" as used herein is understood as a temperature specifically between 15° C. and 30° C., more specifically between 20° C. and 25° C.

The method according to this disclosure may further comprise an additional step e) of applying at least one membrane layer, the membrane layer at least partially covering the working electrode.

The term "membrane layer," as used herein, is a broad term and is to be given its ordinary and customary meaning to a person of ordinary skill in the art and is not to be limited to a special or customized meaning. The term specifically may refer, without limitation, to a layer of at least one material, which provides a selective barrier. Thus, the membrane layer generally may selectively allow for one or more molecules and/or compounds to pass, whereas other molecules and/or compounds are stopped by the membrane layer. Thus, as outlined above, the membrane layer is permeable for the at least one analyte to be detected. Thus, as an example, the membrane layer may be permeable for one or more of blood glucose, lactate, cholesterol or other types of analytes. The at least one membrane layer may hence function as a diffusion barrier that controls diffusion of the analyte from the exterior, e.g., the body fluid surrounding the analyte sensor, to the sensing material, i.e., the enzyme molecules in the sensing material. In addition, the at least one membrane layer may function as a biocompatibility membrane layer as mentioned elsewhere herein.

The membrane layer, as an example, may have a thickness sufficient for providing mechanical stability. The at least one membrane layer specifically may have a thickness of 1 μm to 150 μm. For the at least one membrane layer, as outlined herein, several materials may be used, standalone or in combination. Thus, as an example, the membrane layer specifically may comprise one or more of a polymeric material, specifically a polyvinylpyridine based copolymer, a polyurethane; a hydrogel; a polyacrylate; a methacrylate-acrylate copolymer or block-copolymer; among which polyvinylpyridine based copolymers are particularly suitable. These types of membranes are generally known in the art. As an example, membranes as disclosed in, e.g., EP2697388 A1, WO 2007/071562 A1 and/or in WO 2005/078424 A1 may be used. Specifically, the polymeric material may have a weight average molecular weight (MW) of more than 10.000 kDa. More specifically, the polymeric material may have a weight average molecular weight (MW) of more than 50.000 kDa, or even more than 100.000 kDa. Particularly suitable are polymeric materials with a weight average molecular weight (MW) of 10.000 to 500.000 kDa. The polymeric material of the membrane may be the same as or may be different from the polymeric material of the sensing material.

Moreover, the membrane layer may comprise a cross-linker, specifically a chemical crosslinker or a UV-curable crosslinker. The crosslinker may be suitable for crosslinking at least part of the sensing material. Crosslinkers as specified herein above with respect to the sensing material are generally suitable for use in the membrane layer. Particularly suitable are bi- and/or multivalent epoxide based crosslinkers, for example, bi-and/or trifunctional short chain epoxides. Suitable cross-linkers may have a molar mass in the range of 150 g/mol to 10000 g/mol. A molar mass of the crosslinker as specified above may be beneficial as it enables efficient diffusion into the sensing material. Specific examples of suitable crosslinkers comprised in the membrane layer include: diglycidyl ethers, such as Resorcinol diglycidyl ether, Bisphenol A diglycidyl ether, Diglycidyl 1,2-cyclohexanedicarboxylate, Poly(ethylene glycol) diglycidyl ether, Glycerol diglycidyl ether, 1,4-Butanediol diglycidyl ether, Poly(propylene glycol) diglycidyl ether, Bisphenol diglycidyl ether, Poly(dimethylsiloxane), diglycidyl ether, Neopentyl glycol diglycidyl ether, 1,2,7,8-Diepoxyoctane, 1,3-Glycidoxypropyl-1,1,3,3-Tetramethyldisioxane; triglycidyl ethers, such as N,N-Diglycidyl-4-glycidyloxyaniline, Trimethylolpropane triglycidyl ether; tetraglycidyl ethers such as Tetrakisepoxy cyclosiloxane, Pentaerythritol tetraglycidyl ether, tetraglycidyl-4,4'-methylenebisbenzenamine; particularly Poly(ethylene glycol) diglycidyl ether; N,N-Diglycidyl-4-glycidyloxyaniline.

Specifically, in a step e) of the method according to this disclosure, in addition to the at least one membrane layer, at least a second membrane layer may be applied. Said second membrane layer may be a biocompatibility membrane layer.

The term "biocompatibility membrane layer," also denoted biocompatibility layer, as used herein, relates to a layer, in particular an outmost layer of an analyte sensor or part thereof, consisting of a biocompatible material. Specifically, the biocompatibility layer has a thickness of from 1 μm to 10 μm, in an embodiment of from 3 μm to 6 μm. More specifically, the biocompatibility layer covers the analyte sensor at least partly or completely. Even more specifically, the biocompatibility layer may be the outmost layer of the analyte sensor. Thus, even more specifically, at least a part of the biocompatibility layer contacts a body fluid of a subject. For example, the biocompatibility layer may be not diffusion-limiting for the analyte as specified elsewhere herein. For example, the biocompatibility layer may be not diffusion-limiting for small molecules having a molecular weight of less than 2.000 Da, in an embodiment less than 1.000 Da. For example, the biocompatibility layer may not comprise an added enzyme. For example, the biocompatibility layer may not comprise an added polypeptide. As will be understood by the skilled person, this does not exclude that enzyme or polypeptide molecules diffuse into the biocompatibility layer from adjacent layers, tissues, or body fluids. The term "biocompatible material," as used herein relates to a material suitable for use with living tissue or a living system by not being or being to a reduced extent toxic, injurious, or physiologically reactive and/or causing to a reduced extent or not causing immunological rejection. In an embodiment, the biocompatible material is a material not inducing a bodily response, e.g., an inert material or a material comprising chemical compounds preventing bodily responses from occurring in the vicinity of the biocompatibility layer. In another embodiment, the biocompatible material is a material preventing cells from attaching to said biocompatibility layer. The biocompatibility membrane layer may be or may comprise the following materials: methacrylate based polymers and copolymers, acrylamide-methacrylate based copolymers, biodegradable Polysaccharides such as hyaluronic acid (HA), agarose, dextran and chitosan. Further biocompatible materials are disclosed in WO 2019/166394 A1 and include nonbiodegradable synthetic hydrogels such as hydrogels prepared from the copolymerization of 2-hydroxyethyl methacrylate (HEMA), 2-hydroxypropyl methacrylate (HPMA), acrylamide (AAm), acrylic acid (AAc), N-isopropylacrylamide (NIPAm), and methoxyl poly(ethylene glycol) (PEG) monoacrylate (mPEGMA or PEGMA), with cross-linkers, such as N,N'-methylenebis(acrylamide) (MBA), ethylene glycol diacrylate (EGDA) and PEG diacrylate (PEGDA), Pluronic® polymers with a structure of poly(ethylene oxide) (PEO)-poly(propylene oxide) (PPO)-PEO, chemical cross-linking of modified poly(vinyl alcohol) (PVA), Poly (4vinylpyridine), PEG.

The at least one membrane layer and/or the biocompatibility membrane layer may be applied by techniques known to those skilled in the art, using at least one coating process, specifically a wet-coating process, selected from the group consisting of: e.g., spin-coating; spray-coating; doctor-blading; printing; dispensing; slot-coating; dip-coating. A preferred wet-coating process is dip-coating or spray-coating.

The method according to this disclosure may further comprise at least one diffusion step f) wherein, in the diffusion step the crosslinker comprised in the membrane layer may at least partially diffuse into the sensing material. Diffusion may occur during applying the membrane layer to the sensing material. The diffusion of the crosslinker into the sensing material may allow for at least partial cross linking of the sensing material independent of the presence of a crosslinker in the sensing material during step b) of applying the sensing material to the substrate. This may be advantageous as the presence of a crosslinker in the sensing material during applying of the sensing material to the sensor substrate in step b) is not required and can be avoided. Avoiding the presence of a crosslinker in the sensing material during applying the sensing material to the substrate may have the advantages as specified herein above, namely, e.g., constant viscosity properties of the sensing material during applying to the sensor substrate.

In the method according to this disclosure, the diffusion step may further comprise a swelling of at least a part of the sensing material.

The term "swelling" as used herein is a broad term and is to be given its ordinary and customary meaning to a person of ordinary skill in the art and is not to be limited to a special or customized meaning. The term specifically may refer, without limitation, to the binding of water and/or to the binding of water-soluble solvent such as ethanol, methanol, aceton to a material, specifically to the binding of water and/or of water-soluble solvent to the sensing material. Due to the uptake of water and/or the uptake of water-soluble solvent into the sensing material, diffusion of the crosslinker into the sensing material may advantageously be enabled which may be required for efficient cross linking. Swelling may moreover refer to the uptake of water from the membrane layer.

To allow for sufficient swelling in the method according to this disclosure, the polymeric material in the sensing material may be capable of taking up of at least 10 wt.-% of water and/or solvent from the membrane layer based on the dry weight of the polymeric material within a time frame of several minutes, e.g., 1 to 15 minutes, more specifically at least 20 wt.-%, even more specifically at least 30 wt.-%, even more specifically up to 90 wt %.

This swelling and/or uptake of water and/or solvent is advantageous as diffusing of the crosslinker from the membrane layer into the sensing material may thereby be enabled.

Further, this disclosure relates to an analyte sensor. The analyte sensor comprises at least one sensor substrate comprising at least one first side. The first side comprises at least one conductive trace.

The analyte sensor comprises at least one layer of at least one sensing material disposed onto the first side of the sensor substrate, wherein the sensing material covers at least a portion of the at least one conductive trace. The layer of the sensing material is irradiated with at least one laser beam wherein a first portion of the layer of the sensing material is at least partially removed, such that a second portion of the sensing material covering the conductive trace is preserved on the first side of the sensor substrate. Said second portion of the sensing material in conjunction with the conductive trace, forms at least one working electrode of the analyte sensor.

In particular, the working electrode of the analyte sensor may comprise at least one patterned layer of at least one sensing material disposed onto the first side of the sensor substrate. The patterned layer specifically can be obtained by irradiating the layer of the sensing material and/or the sensor substrate with a laser beam. The patterned layer specifically is the second portion of the sensing layer.

The analyte sensor as described herein may in particular be obtainable by the method according to this disclosure for the preparation of a working electrode on a sensor substrate and a step of providing at least one further electrode, e.g., a counter electrode or a reference electrode or a combined counter/reference electrode.

Moreover, this disclosure relates to the use of the analyte sensor for detecting at least one analyte in a sample; specifically in a sample of a body fluid. More particularly, the analyte sensor is a sensor for continuous glucose measurement.

As used herein, the term "body fluid" relates to all bodily fluids of a subject known to comprise or suspected to comprise the analyte of this disclosure, including interstitial fluid, blood, plasma, lacrimal fluid, urine, lymph, cerebrospinal fluid, bile, stool, sweat, and saliva. Generally, an arbitrary type of body fluid may be used. Preferably, the body fluid is a body fluid which is present in a body tissue of a user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The term "sample" is understood by the skilled person and relates to any subportion of a bodily fluid. Samples can be obtained by well-known techniques including, e.g., venous or arterial puncture, epidermal puncture, and the like.

The term "subject" as used herein is a broad term and is to be given its ordinary and customary meaning to a person of ordinary skill in the art and is not to be limited to a special or customized meaning. The term specifically may refer, without limitation, to a human being or an animal, independent from the fact that the human being or animal, respectively, may be in a healthy condition or may suffer from one or more diseases. As an example, the subject may be a human being or an animal suffering from diabetes. However, additionally or alternatively, this disclosure may be applied to other types of subjects.

Moreover, this disclosure relates to a method for measuring an analyte in a sample comprising the analyte sensor described herein above.

The methods for measuring of an analyte of this disclosure, in particular, may be in vivo methods. Alternatively, the method of this disclosure may also encompass measuring of an analyte under in vitro conditions, e.g., in a sample of a body fluid obtained from a subject, particularly from a human subject. Specifically, said method may not comprise diagnosis of disease based on said measurement.

Summarizing and without excluding further possible embodiments, the following embodiments may be envisaged.

Embodiment 1: A method for the preparation of a working electrode on a sensor substrate, the method comprising:

a) providing at least one sensor substrate comprising at least a first side, the first side comprising at least one conductive trace;

b) applying at least one layer of at least one sensing material onto the first side of the sensor substrate, wherein the sensing material covers at least a portion of the at least one conductive trace; and c) irradiating the layer of the sensing material with at least one laser beam, wherein at least a first portion of the layer of the sensing material is at least partially removed and wherein at least a second portion of the sensing material covering the at least one conductive trace is preserved on the first side of the sensor substrate to obtain at least one working electrode on the sensor substrate.

Embodiment 2: The method according to embodiment 1, wherein the sensing material comprises at least a polymeric material; specifically at least a polymeric material and at least a metal containing complex selected from the group of transition metal element complexes, more specifically a metal containing complex selected from osmium-complexes, ruthenium-complexes, vanadium-complexes, cobalt-complexes, and iron-complexes such as ferrocenes, in particular 2-aminoethylferrocene.

Embodiment 3: The method according to embodiment 1 or 2, comprising an additional step bb) of drying the at least one layer of the at least one sensing material, prior to step c); specifically drying takes place at ambient temperature.

Embodiment 4: The method according to embodiments 1 to 3, wherein the sensing material comprises at least one crosslinker.

Embodiment 5: The method according to embodiment 4, wherein the crosslinker is a chemical crosslinker, specifically selected from epoxide based crosslinkers, such as diglycidyl ethers like poly(ethylene glycol) diglycidyl ether (PEG-DGE) and poly(propylene glycol) diglycidyl ether; trifunctional short chain epoxides.

Embodiment 6: The method according to embodiments 1 to 5, wherein step b) comprises using at least one coating process, specifically a wet-coating process, selected from the group consisting of: spin-coating; spray-coating; doctor-blading; printing; dispensing; slot-coating; dip-coating.

Embodiment 7: The method according to embodiments 1 to 6, wherein the method further comprises:

d) at least one curing step, wherein in the curing step at least a part of the sensing material is cross-linked.

Embodiment 8: The method according to embodiment 7, wherein step d) is performed at least partially after performing step c).

Embodiment 9: The method according to embodiments 1 to 8, further comprising:

e) applying at least one membrane layer, the membrane layer at least partially covering the working electrode, specifically the second portion of the sensing material.

Embodiment 10: The method according to embodiment 9, wherein the membrane layer comprises one or more of a polymeric material, specifically a polyvinylpyridine based copolymer, a polyurethane, a hydrogel; a polyacrylate; a methacrylate-acrylate copolymer or block-copolymer.

Embodiment 11: The method according to embodiment 9 or 10, wherein the membrane layer comprises at least one crosslinker for cross-linking at least a part of the sensing material.

Embodiment 12: The method according to embodiment 11, wherein the method further comprises:

f) at least one diffusion step, wherein in the diffusion step the crosslinker comprised in the membrane layer at least partially diffuses into the sensing material.

Embodiment 13: The method according to embodiment 12, wherein the diffusion step comprises a swelling of at least a part of the sensing material.

Embodiment 14: The method according to embodiments 11 to 13, wherein the crosslinker comprised in the membrane layer comprises at least one bi- and/or multivalent epoxide based crosslinker of low molecular weight, for example, a trifunctional short chain epoxide.

Embodiment 15: The method according to embodiments 10 to 14, wherein the polymeric material in the membrane layer has a molecular weight of more than 10.000 kDa.

Embodiment 16: The method according to embodiments 9 to 15, wherein the membrane layer is applied by dip-coating.

Embodiment 17: The method according to embodiments 1 to 16, wherein the sensing material comprises at least one enzyme; specifically the enzyme is an enzyme capable of catalyzing a chemical reaction consuming at least the analyte, more specifically an $H_2O_2$ generating and/or consuming enzyme, even more specifically a glucose oxidase (EC 1.1.3.4), a hexose oxidase (EC 1.1.3.5), an (S)-2 hydroxy acid oxidase (EC 1.1.3.15), a cholesterol oxidase (EC 1.1.3.6), a galactose oxidase (EC 1.1.3.9), glucose dehydrogenase, an alcohol oxidase (EC 1.1.3.13), an L-glutamate oxidase (EC 1.4.3.11) or an L-aspartate oxidase (EC 1.4.3.16), even more specifically a glucose oxidase and/or modifications thereof.

Embodiment 18: The method according to embodiments 1 to 17, wherein the conductive trace comprises at least one conductive material selected from the group consisting of: carbon; gold; platinum; palladium.

Embodiment 19: The method according to embodiments 1 to 18, wherein the sensor substrate comprises two opposing sides, the first side and at least a second side opposing the first side.

Embodiment 20: The method according to embodiment 18, wherein the conductive trace comprises at least one further layer of at least one further material, specifically the further layer comprises an electrically conductive material, e.g., carbon.

Embodiment 21: The method according to embodiments 1 to 20, wherein the conductive trace, specifically the conductive trace comprising carbon, has a thickness of at least 7 µm, specifically of at least 10 µm.

Embodiment 22: The method according to embodiments 1 to 21, wherein the layer of the sensing material has a thickness of 0.5 to 5 µm, specifically 1 to 4 µm, specifically a dry thickness.

Embodiment 23: The method according to embodiments 1 to 22, wherein step c) comprises laser ablation.

Embodiment 24: A method for the preparation of an analyte sensor comprising the method for the preparation of a working electrode on a substrate according to embodiments 1 to 23 and a step of providing at least one further electrode.

Embodiment 25: The method according to embodiment 24, wherein the at least one further electrode comprises at least one of a reference electrode, a counter electrode and a counter/reference electrode.

Embodiment 26: The method according embodiment 25, wherein the reference electrode comprises at least one reference electrode conductive trace.

Embodiment 27: The method according to embodiment 25 or 26, wherein the counter electrode comprises at least one counter electrode conductive trace.

Embodiment 28: The method according to embodiments 25 to 27, wherein the at least one further electrode is disposed on at least one of: the first side and the second side opposing the first side.

Embodiment 29: An analyte sensor comprising at least one working electrode obtainable by a method according to embodiments 1 to 24 and at least one further electrode.

Embodiment 30: An analyte sensor, comprising:
A) at least one sensor substrate comprising at least one first side, the first side comprising at least one conductive trace;
B) at least one layer of at least one sensing material disposed onto the first side of the sensor substrate, wherein the sensing material covers at least a portion of the at least one conductive trace, and wherein the layer of the sensing material is irradiated with at least one laser beam, wherein a first portion of the layer of the sensing material is at least partially removed, such that a second portion of the sensing material covering the conductive trace is preserved on the first side of the sensor substrate, wherein said second portion of the sensing material in conjunction with the conductive trace, forms at least one working electrode of the analyte sensor.

Embodiment 31: The analyte sensor according to embodiment 30, wherein the working electrode is obtainable by the method according to embodiments 1 to 23.

Embodiment 32: The analyte sensor according to embodiment 30 or 31, wherein the working electrode comprises at least one patterned layer of at least one sensing material disposed onto the first side of the sensor substrate.

Embodiment 33: Use of the analyte sensor according to embodiments 29 to 32, for detecting at least one analyte in a sample, specifically in a sample of a body fluid.

Embodiment 34: Method for measuring an analyte in a sample comprising the analyte sensor according to embodiments 29 to 32.

Embodiment 35: Analyte sensor obtainable by a method according to embodiments 24 to 28.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 is a schematic cross sectional view of at least one analyte sensor according to this disclosure depicting layers in a sensor substrate;

FIG. 2 is a schematic cross sectional view of the layers of the analyte sensor depicting the sensor substrate with sensing material prior to laser ablation;

FIG. 3 is a schematic cross sectional view of the analyte sensor depicting the sensor substrate with the sensing layer after laser ablation;

FIG. 4 is a flow chart depicting the method steps according to this disclosure;

DESCRIPTION

Figure 5:
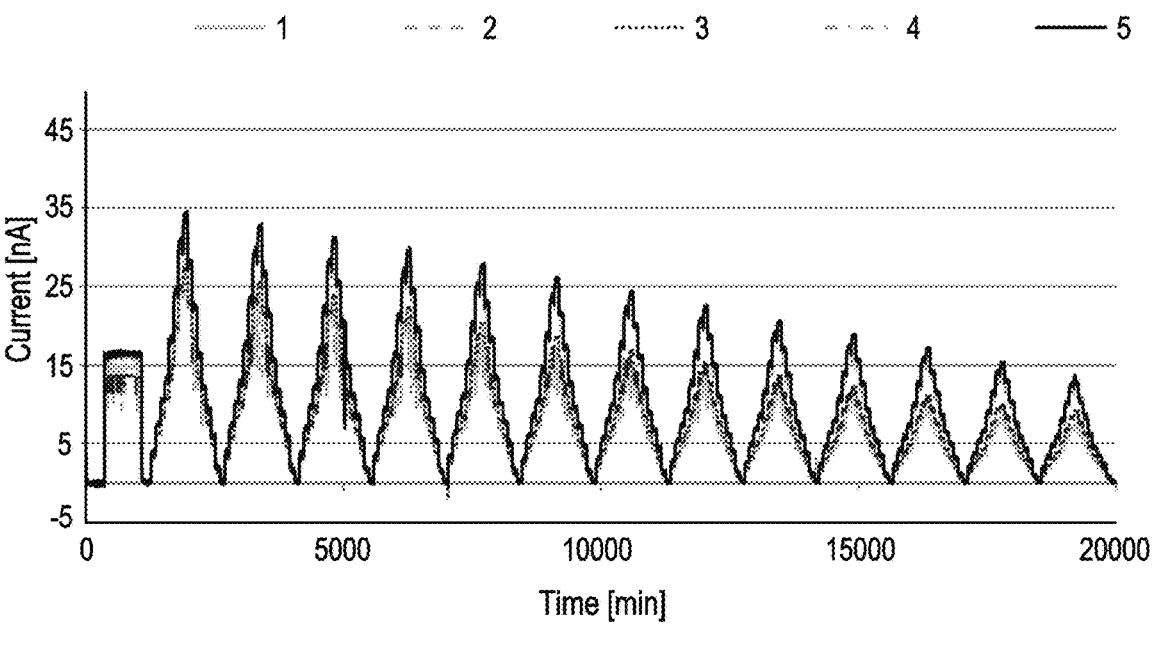
FIG. 5 depicts the sensor performance of sensors prepared without laser ablation.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

FIGS. 1 to 3 show intermediate products in the method for the preparation of the analyte sensor 124. FIG. 4 gives a schematic overview of the steps of the method according to this disclosure. In the following, these figures will be explained jointly.

FIG. 1 shows the at least one sensor substrate 114 of the at least one analyte sensor 124 comprising at least one first side 120. The first side 120 comprises at least one conductive trace 111. The analyte sensor 124 comprises at least one layer of at least one sensing material 118 disposed onto the first side 120 of the sensor substrate 114 as shown in FIGS. 2 and 3. The sensing material 118 covers at least a portion of the at least one conductive trace 111. As shown in FIG. 3, the layer of the sensing material 118 is laser-irradiated with at least one laser beam 126, such that a portion of the sensing material 118 covering the conductive trace 111 is preserved on the first side of the sensor substrate. Said portion of the sensing material in conjunction with the conductive trace 111, forms at least one working electrode 122 of the analyte sensor 124. In particular, the working electrode 122 of the analyte sensor may comprise at least one patterned layer 128 of at least one sensing material disposed onto the first side of the sensor substrate. The patterned layer 128 specifically can be obtained by irradiating the layer of the sensing material 118 and/or the sensor substrate 114 with a laser beam 126. The patterned layer 128 is then the second portion which was not irradiated.

The analyte sensor 124 specifically may be an analyte sensor 124 suitable for at least partial implantation into a body tissue of a user, more specifically an analyte sensor for continuous monitoring of the analyte. The analyte sensor 124 may in particular be obtainable by the method according to this disclosure.

Moreover, the analyte sensor 124 is an electrochemical sensor comprising at least one electrode and respective circuitry. More particularly, the analyte sensor 124 is an amperometric electrochemical sensor comprising the at least one working electrode. Typically, the analyte sensor 124 comprises at least one further electrode, particularly a counter electrode and/or a reference electrode. The working electrode 122 may be sensitive for the analyte to be measured at a polarization voltage which may be applied between working and reference electrodes and which may be regulated by a potentiostat. A measurement signal may be provided as an electric current between the counter electrode and the working electrode. A separate counter electrode may be absent and a pseudo reference electrode may be present, which may also work as a counter electrode. Thus, an analyte sensor 124 typically may comprise a set of at least two or a set of three electrodes. Specifically, the sensing material 118 is present in the working electrode 122 only.

In particular, the working electrode 122 may be disposed on the at least one sensor substrate 114 comprising the at least one first side 120. The first side 120 may comprise at least one conductive trace 111 and at least one layer of at least one sensing material 118 disposed onto the first side of the sensor substrate 114. The sensing material 118 may cover at least a portion of the at least one conductive trace 111. The layer of the sensing material 118 may be laser-irradiated with at least one laser beam wherein a first portion of the layer of the sensing material 118 is at least partially removed, such that a second portion of the sensing material 118 covering the conductive trace 111, is preserved on the first side of the sensor substrate. Said second portion of the sensing material in conjunction with the conductive trace 111 forms at least one working electrode 122 of the analyte sensor 124. The layer of sensing material 118 may be present on the working electrode only and may typically be absent from any further electrodes, e.g., the counter electrode and/or the reference electrode may not comprise a layer of the sensing material 118.

Specifically, the analyte sensor 124, more specifically the sensor substrate 114, may additionally comprise at least one further electrode, wherein the at least one further electrode may comprise at least one of a reference electrode and a counter electrode. In particular, the reference electrode may comprise at least one reference electrode conductive trace; and or the counter electrode may comprise at least one counter electrode conductive trace.

The at least one conductive trace 111 may comprise at least one material selected from the group consisting of: carbon; carbon paste; gold; copper; silver; nickel; platinum; palladium. Specifically, the conductive trace 111 may be or may comprise at least one metal, such as one or more of gold, copper, silver, nickel, palladium or platinum. Additionally or alternatively, the at least one conductive trace 111 may be or may comprise at least one electrically conductive compound, such as at least one electrically conductive organic or inorganic compound. Additionally or alternatively, the conductive trace 111 may be or may comprise at least one nonmetallic electrically conductive material, e.g., carbon or carbon paste. Preferably, the conductive trace 111 according to this disclosure may comprise gold and/or carbon; more preferably the conductive trace may consist of gold 112 and/or carbon 110. Specifically, the conductive trace may comprise gold 112 and a further material, for example, carbon 110.

Moreover, the conductive trace 111 may comprise at least one further layer of at least one further material, specifically the further layer may comprise a further electrically conductive material. More specifically the further layer of the conductive trace may comprise or may consist of carbon 110. Using a further layer comprising or consisting of carbon 110 in the conductive trace 111 on the sensor substrate may be advantageous as it may enhance the attachment of the layer of the sensing material 118 on the conductive trace 111.

The sensing material 118 may be or may comprise at least a polymeric material; specifically it may be or may comprise at least a polymeric material and at least a metal containing complex. The metal containing complex may be selected from the group of transition metal element complexes, specifically the metal containing complex may be selected from osmium-complexes, ruthenium-complexes, vanadium-complexes, cobalt-complexes, and iron-complexes, such as ferrocenes, particularly 2-aminoethylferrocene. In particular, the sensing material 118 may comprise a modified poly (vinylpyridine) backbone loaded with poly(bi-imidizyl) Os complexes covalently coupled through a bidentate linkage.

The sensing material 118 may at least comprise a polymeric transition metal complex, an enzyme capable of catalyzing a chemical reaction consuming at least the analyte, particularly an $H_2O_2$ generating and/or consuming enzyme 116, and optionally a crosslinker. Specifically, the sensing material 118 may comprise at least a polymeric transition metal complex and GOx and optionally a chemical crosslinker. More specifically, the sensing material 118 may comprise a modified poly (vinylpyridine) backbone loaded with poly(bi-imidizyl) Os complexes covalently coupled through a bidentate linkage, GOx and optionally a chemical crosslinker.

The sensing material may 118, in addition, comprise at least one enzyme 116; specifically the enzyme is capable of catalyzing a chemical reaction consuming at least the analyte, more specifically the enzyme may be a $H_2O_2$ generating and/or consuming enzyme, even more specifically a glucose oxidase (EC 1.1.3.4), a hexose oxidase (EC 1.1.3.5), an (S)-2 hydroxy acid oxidase (EC 1.1.3.15), a cholesterol oxidase (EC 1.1.3.6), glucose dehydrogenase, a galactose oxidase (EC 1.1.3.9), an alcohol oxidase (EC 1.1.3.13), an L-glutamate oxidase (EC 1.4.3.11) or an L-aspartate oxidase (EC 1.4.3.16); even more specifically a glucose oxidase (GOx) and/or modifications thereof.

Moreover, the sensing material 118 may additionally comprise at least one crosslinker; the crosslinker may, for example, cross link at least part of the sensing material 118. Specifically the sensing material 118 may comprise at least one crosslinker selected from UV-curable crosslinkers and chemical crosslinkers; more specifically the sensing material 118 comprises a chemical crosslinker. Alternatively, the sensing material 118 may be free of any crosslinker.

A flow chart of the method according to this disclosure is depicted in FIG. 4. The method comprises the following steps:

a) providing at least one sensor substrate 114 comprising at least a first side 120, the first side 120 comprising at least one conductive trace 111 (130);

b) applying at least one layer of at least one sensing material 118 onto the first side 120 of the sensor substrate 114, wherein the sensing material 118 covers at least a portion of the at least one conductive trace 111 (132); and c) irradiating the layer of the sensing material 118 with at least one laser beam 126, wherein at least a first portion of the layer of the sensing material is at least partially removed and wherein at least a second portion of the sensing material covering the at least one conductive trace is preserved on the first side of the sensor substrate to obtain at least one working electrode 122 on the sensor substrate 114.

By irradiating the sensing material 118 with the laser beam 126 (134) the first portion may be ablated from the layer of the sensing material 118 thereby generating or forming a patterned layer 128 on the sensor substrate 114.

This disclosure is not limited to one of the embodiments described above, but is modifiable in a great variety of ways. Those skilled in the art recognize that the embodiments according to this disclosure, can easily be adapted without departing from the scope of this disclosure. Thus simple adaptations are conceivable for the preparation of the analyte sensor. This disclosure enables the preparation of an analyte with reproducible sensor sensitivity at reduced production costs. Further characteristics, details and advantages of this disclosure follow from the wording of the claims and from the following description of practical examples on the basis of the drawings.

The content of all literature references cited in this patent application is hereby included by reference to the respective specific disclosure content and in its entirety.

EXAMPLES

The following examples serve to illustrate this disclosure. They must not be interpreted as limiting with regard to the scope of protection.

Example 1

Preparation of the Layer of Sensing Material of a Working Electrode

A sensor substrate as depicted schematically in FIG. 1 based on Polyethylene terephthalate and a thin layer of gold was coated with a carbon paste via doctor blading. Suitable carbon conductive inks are available from Ercon, Inc. (Wareham, MA), E.I. du Pont de Nemours and Co. (Wilmington, DE), Emca-Remex Products (Montgomeryville, PA), or TEKRA, A Division of EIS, Inc. (New Berlin, WI).

Afterwards the carbon paste was dried for 12 h at 50° C. The enzyme- and mediator-containing formulation that can be used in the sensing layer, are known in the art, for ex-ample, from "A Continuous Glucose Sensor Based on Wired Enzyme™ Technology—Results from a 3-Day Trial in Patients with Type 1 Diabetes." DIABETES TECH-NOLO-GY & THERAPEUTICS Volume 5, Number 5, 2003 approx. 35% (by weight) redox polymer, 40% GOx, and 25% cross-linker were used or approx. 50% (by weight) redox polymer, 50% GOx.

The layer of sensing material applied on the sensor substrate by cannula coating (PTFE cannula 1.6 mm, Flow Rate 0.09 ml/min, Speed 8 mm/s. The sensing material was dried for 10 minutes at room temperature. Thereby obtaining a layer set up as depicted schematically in FIG. 2.

Example 2

Structuring of the Layer of Sensing Material Using Laser Ablation

Following drying, the sensor element obtained in example 1 was further structured and cut using a laser beam. The conditions shown in Table 1 for the laser system 3D Micro-mac microCut TMS; UKP-Laser Hyper Rapid 50-SW 355 were used.

A schematic representation of the layers of the analyte after laser ablation is depicted in FIG. 3.

TABLE 1

| Conditions for laser system | | |
| --- | --- | --- |
| Process | Laser ablation Os-Chemistry | Cut |
| Power (Counts \| Measured value in W) | 510 Counts = 1.19 W | 800 Counts |
| Pulse rate/kHz | 400 | 400 |
| Number of Repetition | 1 | 5 |

Example 3

Application of the Membrane Layers

The membrane polymer 15% (w/v) Poly (4-(N-(3-sulfonatopropyl)-pyridinium)-co-pyridine-co-styrene) was dissolved in ethanol/water (80/20) and mixed until a brown solution obtained. The crosslinker 3.75% (w/v) Glycerol triglycidyl ether crosslinker solution was dissolved in etha-nol/water (80/20) and mixed until a clear solution obtained. The membrane polymer and crosslinker solution were mixed (4:1). The laser ablated sensor was dip coated 3 times in the membrane polymer/cross-linker solution as described in "Miniature Amperometric Self-Powered Continuous Glu-cose Sensor with Linear Response" Anal. Chem. 2012, 84, 7, 3403-3409 Publication Date: Mar. 14, 2012.

Example 4

Determination of Sensor Performance

Both sensor types (with structuring by laser ablation according to example 2 and without structuring according to example 1) were analyzed using a potentiostat in a chrono-amperometric setup. The potential was 50 mV against Ag/AgCl as a reference electrode. The measurements were performed over 14 days at different glucose levels c(Glu-kose) (concentration glucose) in mg/dl: 0; 14,4; 36; 54; 72; 90; 108; 126; 144; 180; 216; 270; 306; 360; 414; 468. Each step lasted for approx. 90 minutes and after one day the glucose level measurements were repeated.

Figure 6:
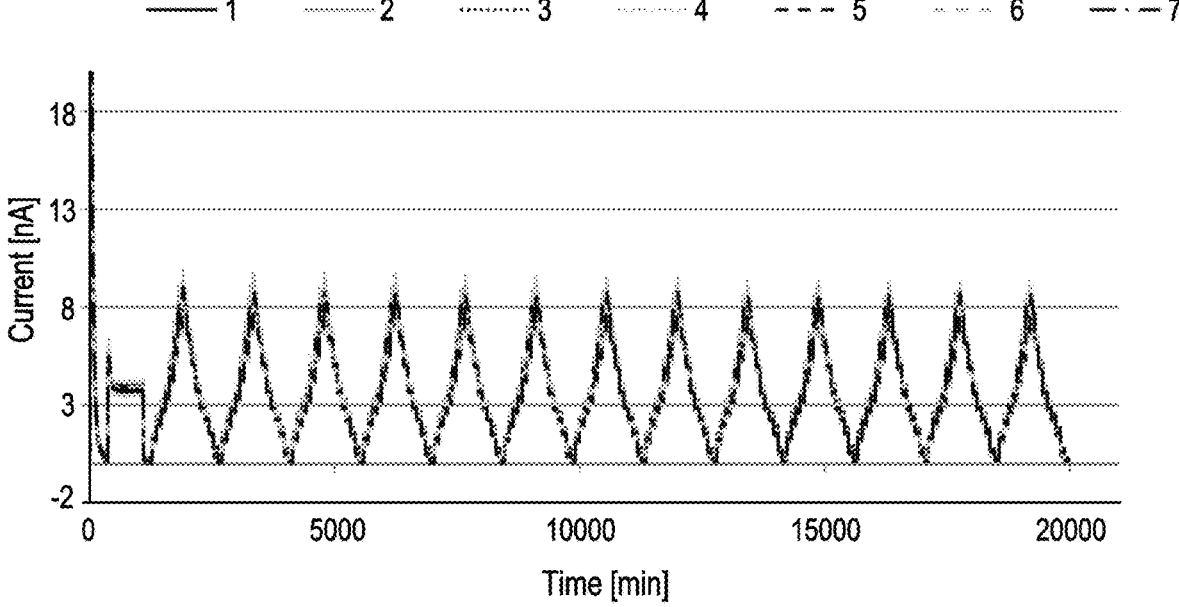
FIG. 6 depicts the sensor performance of sensors prepared with laser ablation.

The sensor performance of sensors prepared without laser ablation (5 sensors; n=5) is shown in FIG. 5 and in Table 2; the sensor performance of sensors prepared with laser abla-tion (7 sensors; n=7) is shown in FIG. 6 and in Table 3.

TABLE 2

| Results of sensors prepared without laser ablation (Example 1) | | | | |
| --- | --- | --- | --- | --- |
| Time [d] | Median Sensitivity [nA/mM] Sensor 1-5 | Standard Deviation Sensitivity [nA/mM] Sensor 1-5 | Relative Standard Deviation [%] Sensor 1-5 | Median Drift [%]/Day @ 10 mM Sensor 1-5 | Standard Deviation Drift [%] Sensor 1-5 |
| 1 | 1.35 | 0.16 | 12 | — | — |
| 2 | 1.25 | 0.17 | 14 | −7 | 2 |
| 3 | 1.15 | 0.18 | 16 | −8 | 3 |
| 4 | 1.08 | 0.19 | 17 | −6 | 1 |
| 5 | 0.99 | 0.21 | 21 | −9 | 4 |
| 6 | 0.91 | 0.21 | 23 | −8 | 2 |
| 7 | 0.82 | 0.22 | 26 | −10 | 3 |
| 8 | 0.74 | 0.21 | 28 | −10 | 1 |
| 9 | 0.66 | 0.20 | 30 | −10 | 1 |
| 10 | 0.59 | 0.18 | 31 | −10 | 2 |
| 11 | 0.54 | 0.17 | 32 | −10 | 1 |
| 12 | 0.48 | 0.15 | 31 | −11 | 1 |
| 13 | 0.43 | 0.11 | 26 | −10 | 6 |

TABLE 3

| | Median Sensitivity [nA/mM] Sensor 1-7 | Standard Deviation Sensitivity [nA/mM] Sensor 1-7 | Relative Standard Deviation [%] Sensor 1-7 | Median Drift [%]/Day @ 10 mM Sensor 1-7 | Standard Deviation Drift [%] Sensor 1-7 |
|---|---|---|---|---|---|
| Time [d] | | | | | |

Results of sensors prepared with laser ablation (Example 2)

| Time [d] | Median Sensitivity [nA/mM] Sensor 1-7 | Standard Deviation Sensitivity [nA/mM] Sensor 1-7 | Relative Standard Deviation [%] Sensor 1-7 | Median Drift [%]/Day @ 10 mM Sensor 1-7 | Standard Deviation Drift [%] Sensor 1-7 |
|---|---|---|---|---|---|
| 1 | 0.35 | 0.02 | 5.7 | — | — |
| 2 | 0.35 | 0.02 | 5.9 | 0.1 | 0.4 |
| 3 | 0.35 | 0.02 | 5.8 | 0.3 | 0.3 |
| 4 | 0.35 | 0.02 | 5.7 | −0.7 | 0.4 |
| 5 | 0.36 | 0.02 | 5.5 | −0.4 | 0.8 |
| 6 | 0.35 | 0.02 | 5.5 | −1.1 | 0.9 |
| 7 | 0.35 | 0.02 | 5.8 | 0.3 | 0.7 |
| 8 | 0.35 | 0.02 | 5.7 | −0.2 | 0.4 |
| 9 | 0.35 | 0.02 | 5.4 | −0.8 | 0.3 |
| 10 | 0.35 | 0.02 | 5.2 | 0.2 | 0.3 |
| 11 | 0.35 | 0.02 | 4.9 | −0.2 | 0.4 |
| 12 | 0.35 | 0.02 | 5.0 | 0.0 | 0.7 |
| 13 | 0.35 | 0.02 | 4.8 | −0.1 | 0.5 |

The sensors with laser ablation have a reduced sensitivity in contrast to the non-laser ablated sensors due to the ablated sensing material, but the ablated sensors have significantly reduced relative standard deviation and significantly reduced drift due to the homogeneous thickness and area of the sensing material.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

110 Carbon
111 Conductive trace
112 Gold
114 Sensor substrate
116 Enzyme
118 Sensing material
120 First side
122 Working electrode
124 Analyte sensor
126 Laser beam
128 Patterned layer
130 Step a) providing at least one sensor substrate
132 Step b) applying at least one layer of at least one sensing material
134 Step c) irradiating the layer of the sensing material with at least one laser beam

What is claimed is:

1. A method of preparing a working electrode on a sensor substrate, comprising:
a) providing a sensor substrate having a first side with at least one conductive trace;
b) applying a layer of sensing material having an un-crosslinked polymeric material onto the first side, wherein the sensing material covers at least a portion of the at least one conductive trace; and
c) irradiating the layer of the sensing material with a laser beam, wherein at least a first portion of the layer of the sensing material is at least partially removed and wherein at least a second portion of the sensing material covering the at least one conductive trace is preserved on the first side of the sensor substrate to obtain a working electrode on the sensor substrate;
d) applying a membrane layer that at least partially covers the working electrode, wherein the membrane layer comprises a cross-linker configured for cross-linking to the un-crosslinked polymeric material of the sensing material; and
e) a diffusion step in which the cross-linker in the membrane layer at least partially diffuses into the sensing material.

2. The method according to claim 1, comprising an additional step bb) of drying the layer of the sensing material, prior to step c).

3. The method according to claim 1, further comprising a curing step in which at least a part of the sensing material is cross-linked.

4. The method according to claim 3, wherein the curing step is performed at least partially after performing step c).

5. The method according to claim 1, wherein the cross-linker in the membrane layer comprises at least one bi- and/or multivalent epoxide based cross-linker.

6. The method according to claim 1, wherein the conductive trace comprises at least one conductive material selected from the group consisting of: carbon; gold; copper; silver; nickel; platinum; palladium.

7. The method according to claim 6, wherein the conductive trace comprises at least one further layer of at least one further material.

8. The method according to claim 1, wherein the conductive trace has a thickness of at least 7 μm.

9. An analyte sensor comprising at least one working electrode obtained by the method according to claim 1 and comprising at least one further electrode.

10. The method according to claim 1, wherein the un-crosslinked polymeric material includes a modified poly(vinylpyridine) backbone.

11. An analyte sensor, comprising:
A) a sensor substrate having a first side with at least one conductive trace;
B) a layer of sensing material disposed on the first side, wherein the sensing material includes an un-crosslinked polymeric material comprising modified poly(vinylpyridine) backbone, and covers at least a portion of the at least one conductive trace, and wherein the layer of the sensing material is irradiated with at least one laser beam such that the first portion of the layer of the sensing material is at least partially removed and a second portion of the sensing material covering the conductive trace is preserved on the first side of the sensor substrate, wherein said second portion of the sensing material in conjunction with the conductive trace, forms a working electrode of the analyte sensor.

12. Use of the analyte sensor according to claim 11 for detecting at least one analyte in a sample.

* * * * *